(12) United States Patent
O'Rourke

(10) Patent No.: US 8,439,844 B2
(45) Date of Patent: May 14, 2013

(54) STEP RATE OPTIMIZATION DEVICE

(75) Inventor: Michael F. O'Rourke, Hunters Hill (AU)

(73) Assignee: Aortic Wrap Pty Ltd., Darlinghurst, NSW (AU)

( * ) Notice: Subject to any disclaimer, the term of this patent is extended or adjusted under 35 U.S.C. 154(b) by 526 days.

(21) Appl. No.: 12/666,316

(22) PCT Filed: Jun. 2, 2008

(86) PCT No.: PCT/AU2008/000789
§ 371 (c)(1), (2), (4) Date: Dec. 23, 2009

(87) PCT Pub. No.: WO2009/003212
PCT Pub. Date: Jan. 8, 2009

(65) Prior Publication Data
US 2010/0189209 A1 Jul. 29, 2010

(30) Foreign Application Priority Data
Jul. 2, 2007 (AU) ................ 2007903559

(51) Int. Cl.
*A61B 5/0205* (2006.01)
*A61B 5/02* (2006.01)
(52) U.S. Cl.
USPC ........................ 600/483; 600/587; 600/595
(58) Field of Classification Search ............... 600/483, 600/587, 595
See application file for complete search history.

(56) References Cited

U.S. PATENT DOCUMENTS

| | | | |
|---|---|---|---|
| 5,158,091 A * | 10/1992 | Butterfield et al. | ........... 600/485 |
| 6,473,483 B2 | 10/2002 | Pyles | |
| 7,034,694 B2 * | 4/2006 | Yamaguchi et al. | ....... 340/573.1 |
| 2004/0106872 A1 | 6/2004 | Kosuda | |

FOREIGN PATENT DOCUMENTS

WO    2007053892    5/2007

OTHER PUBLICATIONS

"Improved Cardiovascular Performance with Optimal Entrainment Between Heart Rate and Step Rate During Running in Humans", Michael O'Rourke, MD and Alberto Avolio, PhD; Coronary Artery Disease 1992, 3:863-869.
"McDonald's Blood Flow in Arteries—Theoretical, Experimental and Clinical Principles", Sixth Edition, 2011, Wilmer W. Nichols et al., pp. 553-558.
"The Rhythm of Running: Can the Heart Join In?", O'Rourke et al., Aust NZ Med 1993; 23:708-710.

* cited by examiner

*Primary Examiner* — Michael Kahelin
*Assistant Examiner* — Yunqing Wang
(74) *Attorney, Agent, or Firm* — Andrus, Sceales, Starke & Sawall, LLP

(57) ABSTRACT

A step rate optimization device (12). The device includes a timer, a pedometer, an arterial waveform sensor (24), a processor and an indicator (16). The device indicates to the user (10) of a substantially sub-optimal relationship between the user's pulse rate and stride rate when the user's dominant stride rate frequency is at about 2-3 Hz and has a larger amplitude than the component of the user's dominant pulse waveform frequency at about 4-7 Hz and of a substantially optimal relationship between the user's pulse rate and stride rate when the user's dominant stride rate frequency component is at about 4-7 Hz and has a larger amplitude than the component of the user's dominant pulse waveform frequency at about 2-3 Hz.

16 Claims, 5 Drawing Sheets

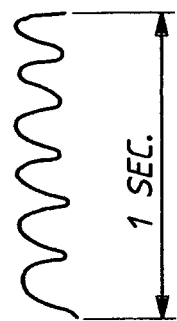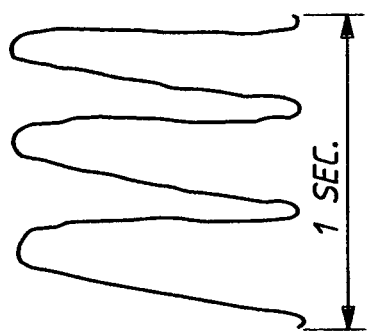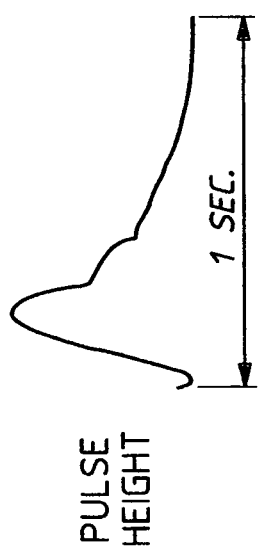

STEP RATE OPTIMIZATION DEVICE

CROSS REFERENCE TO RELATED APPLICATION

The present application is the U.S. national stage application of International Application PCT/AU2008/000789, filed Jun. 2, 2008, which international application was published on Jan. 8, 2009 as International Publication WO 2009/003212. The International Application claims priority of Australian Patent Application 2007903559, filed Jul. 2, 2007.

FIELD OF THE INVENTION

The present invention relates to a step (stride) rate optimization device and a method for indicating an optimal step (stride) rate.

The invention has been primarily developed for use in optimizing a runner's training and will be described hereinafter with reference to this application. However, the invention is not limited to this particular use and is also suitable for use in indicating the effects of stimuli through the body of a regular nature, such as running or industrial vibrations of a similar rate to running, and identifying cardiovascular related complications during running.

BACKGROUND OF THE INVENTION

The Applicant's International PCT patent application no. PCT/AU2006/001668 ("the PCT application") discloses devices for, and methods of, indicating a relationship between heart rate and external stimuli which are suitable for use in step rate optimization. The disclosure of the PCT application is incorporated herein.

It is an object of the present invention to provide improved devices for, and methods of, step rate optimization.

SUMMARY OF THE INVENTION

Accordingly, in a first aspect, the present invention provides a step rate optimization device, the device comprising:
  a timer adapted to measure a predetermined period of time and issue a first signal indicative thereof;
  a pedometer adapted to measure the number of a user's steps over the predetermined period of time and issue a second signal indicative thereof;
  an arterial waveform sensor adapted to issue a third signal indicative of the user's arterial pulse waveform over the predetermined period of time;
  a processor adapted to receive said first, second and third signals and determine and issue a fourth signal indicative of the user's dominant stride rate frequency, the user's dominant pulse rate waveform frequency and the interaction of the user's dominant stride rate frequency and the user's dominant pulse rate waveform frequency in the range of approximately 0-8 Hz; and
  an indicator adapted to indicate to the user a display indicative of a substantially sub-optimal relationship between the user's pulse rate and stride rate when the fourth signal indicates the user's dominant stride rate frequency to be at about 2-3 Hz and having a larger amplitude than the component of the user's dominant pulse waveform frequency at about 4-7 Hz and a display indicative of a substantially optimal relationship between the user's pulse rate and stride rate when the fourth signal indicates the user's dominant stride rate frequency component to be at about 4-7 Hz and having a larger amplitude than the component of the user's dominant pulse waveform frequency at about 2-3 Hz.

The third signal is preferably indicative of the user's arterial pulse waveform frequency and amplitude over the predetermined period of time.

The indicator is preferably adapted to indicate to the user a display indicative of a substantially sub-optimal relationship between the user's pulse rate and stride rate when the fourth signal indicates the user's dominant stride rate frequency to be at about 3 Hz and having a larger amplitude than the component of the user's dominant pulse waveform frequency at about 6 Hz and a display indicative of a substantially optimal relationship between the user's pulse rate and stride rate when the fourth signal indicates the user's dominant stride rate frequency component to be at about 6 Hz and having a larger amplitude than the component of the user's dominant pulse waveform frequency at about 3 Hz.

Preferably, the processor is further adapted to determine that the amplitude of the user's dominant pulse waveform whilst in the optimal relationship is minimal, most preferably less than about 33%, compared to the amplitude of the user's dominant pulse waveform whilst in the sub-optimal relationship.

In one form, the indicator is a visual indicator, such as a display screen or differently colored pair of lights each adapted to signal a sub-optimal or optimal relationship. In another form, the indicator is an aural indicator, such as an ear-piece or other speaker.

The user's arterial pulse waveform is preferably measured at the upper body or an upper limb. In one form, the user's arterial pulse waveform is measured by a photo plethysmograph, most preferably on a finger. In another form, the user's arterial pulse waveform is measured by an arterial tonometer, most preferably on a wrist. Pressure, flow or diameter signals may be used to determine the user's arterial pulse waveform frequency and amplitude.

The processor preferably determines the fourth signal by frequency spectrum analysis of the user's arterial pulse waveforms. The predermined period of time is preferably about 30 seconds. The display preferably includes modulus of frequency components over a range of 0.02-8.0 Hz.

The device is preferably adapted to continuously measure the predetermined period of time and continuously issue the display indicative of the relationship between the user's heart rate and stride rate.

In a second aspect, the present invention provides a method for indicating an optimal step rate to a user, the method comprising the following steps:
  a. measuring a predetermined period of time and issuing a first signal indicative thereof;
  b. measuring the number of the user's steps over the predetermined period of time and issuing a second signal indicative thereof;
  c. sensing the user's arterial waveform and issuing a third signal indicative of the user's arterial pulse waveform over the predetermined period of time; and
  d. processing said first, second and third signals and determining and issuing a fourth signal indicative of the user's dominant stride rate frequency, the user's dominant pulse rate waveform frequency and the interaction of the user's dominant stride rate frequency and the user's dominant pulse rate waveform frequency in the range of approximately 0-8 Hz;
  e. indicating to the user a display indicative of a sub-optimal relationship between the user's pulse rate and stride rate when the fourth signal indicates the user's dominant stride rate frequency to be at about 2-3 Hz and having a larger amplitude than the component of the user's dominant pulse waveform frequency at about 4-7 Hz; and f. indicating to the user a display indicative of a substantially optimal relationship between the user's pulse rate and stride rate when the fourth signal indicates the user's dominant stride rate frequency component to be at about 4-7 Hz and having a larger amplitude than the component of the user's dominant pulse waveform frequency at about 2-3 Hz.

Step c. preferably includes issuing the third signal indicative of the user's arterial pulse waveform frequency and amplitude over the predetermined period of time.

Step e. preferably comprises indicating to the user a display indicative of a sub-optimal relationship between the user's pulse rate and stride rate when the fourth signal indicates the user's dominant stride rate frequency to be at about 3 Hz and having a larger amplitude than the component of the user's dominant pulse waveform frequency at about 6 Hz, and step f. preferably comprises indicating to the user a display indicative of a substantially optimal relationship between the user's pulse rate and stride rate when the fourth signal indicates the user's dominant stride rate frequency component to be at about 6 Hz and having a larger amplitude than the component of the user's dominant pulse waveform frequency at about 3 Hz.

The method preferably further comprises determining that the amplitude of the user's dominant pulse waveform whilst in the optimal relationship is minimal, most preferably less than about 33%, compared to the amplitude of the user's dominant pulse waveform whilst in the sub-optimal relationship.

The user's indication is preferably visual indicator, such as via a display screen or differently colored pair of lights each adapted to signal a sub-optimal or optimal condition. In another form, the indication is aural, such as via an ear-piece or other speaker.

The processing step preferably determines the fourth signal by frequency spectrum analysis of the user's arterial pulse waveforms. The predetermined period of time is preferably about 30 seconds. The display preferably includes modulus of frequency components over a range of 0.02-8.0 Hz.

The method preferably further comprises continuously measuring the predetermined period of time and continuously issuing the display indicative of the relationship between the user's heart rate and stride rate.

BRIEF DESCRIPTION OF THE DRAWINGS

A preferred embodiment of the invention will now be described, by way of an example only, with reference to the accompanying drawings in which:

FIG. 3 is a plot of a person's arterial waveform pulse height whilst at rest over a one second interval;

FIG. 4 is a plot of a person's arterial waveform pulse height whilst running with pulse rate and step rate in an unfavourable phase over a one second interval;

FIG. 5 is a plot of a person's arterial waveform pulse height whilst running with pulse rate and step rate in a favourable phase over a one second interval;

DETAILED DESCRIPTION OF THE PREFERRED EMBODIMENT

By way of further background, in long distance running, the arterial pulse waveform contains impulses created by cardiac ejection and also by upward movement of the body caused by the left foot, and then the right foot, striking the ground. Entrainment is reached when the heart rate and step rate occur at the same frequency in the range of 2-3 Hz (120-180/min). When this occurs, all arterial pulse waveforms are identical over a prolonged period.

A runner's training effectiveness is optimised (favourable) if entrainment occurs when the pulse rate and step rate are 180° out of phase, and fluctuations in the arterial pulse are of a minimum amplitude at a frequency of about 2-3 Hz, but dominant at a frequency of twice the heart and step rate (4-6 Hz or 240-360/min).

A runner's training effectiveness is sub-optimal (unfavourable) if entrainment occurs when the pulse rate and step rate are in phase, and fluctuations in the arterial pulse are of a maximal amplitude with a dominant frequency at the heart and step rate (2-3 Hz or 120-180/min).

Before entrainment is reached, a beating phenomenon is seen (see FIG. 10) where there are periods of maximal amplitude of the pulse waveform at frequency 2-3 Hz alternating with periods of minimal amplitude of the pulse waveform at frequency 4-6 Hz. The beating frequency is the difference between pulse (i.e. heart) rate and stride rate frequencies.

Figures 1, 2:
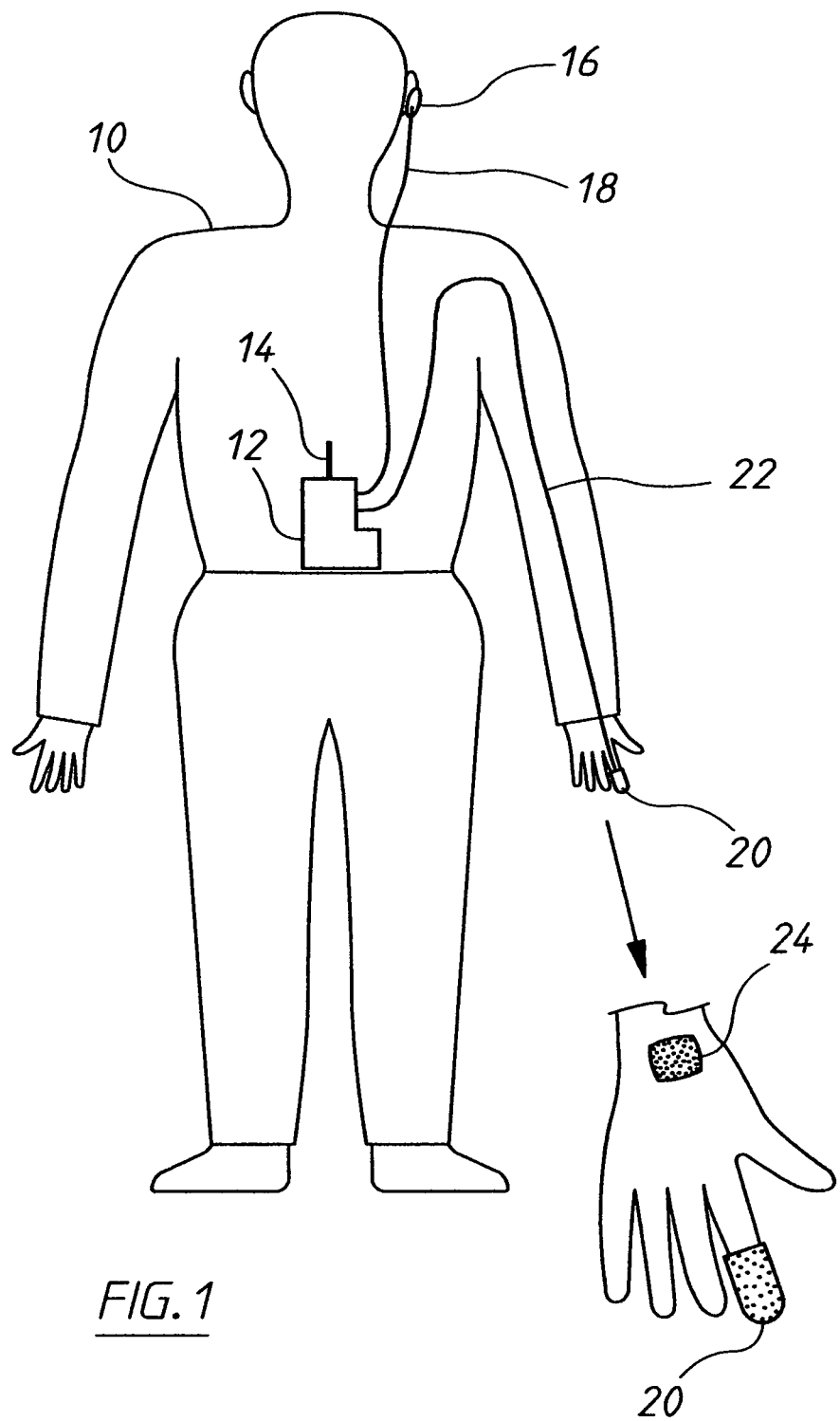
FIG. 1 is a schematic view of a person wearing an embodiment of a step rate optimization device.
FIG. 2 is an enlarged detailed view of the person shown in FIG. 1 showing embodiments of arterial waveform sensors.

FIG. 1 shows a user 10 wearing an embodiment of a step rate optimization device 12. The device 12 contains a timer or clock, a pedometer, a processor, a display screen, a battery (or other power source), an aerial 14 and an indicator in the form of an ear-piece 16 connected to the device 12 by wire 18. The device 12 also includes a pulse waveform sensor in the form of a finger photo plethysmograph 20 connected thereto by wire 22. Alternatively, a radial sensor 24, or other arterial sensor can be used.

The device 12 is attached to the user's torso, or alternatively worn on a belt. The waveform sensor (plethysmograph 20) records frequencies from 0.02 to 8.0 Hz and sends these signals to the processor in the device 12. The processor generates voice messages which are communicated to the user 10 via the earpiece 16. Alternatively, a visual signal may be generated by the processor and transmitted to a screen (e.g. on a treadmill) or to optical devices worn by the user 10 or viewed by a trainer.

The pedometer in the device 12 generates an electric signal as the user's body is elevated with each stride and also sends these signals to the processor. These signals become the reference for frequency spectrum analysis, as will be discussed in more detail below.

The device 12 is set into operation by the user 10 when he/she attains a regular rhythm. At this stage, calibration of stride rate is calculated over a set distance (e.g. 400 meters) by determining the time taken with the clock and the number of strides with the pedometer and supplying this information to the processor. Stride rate can also be signalled to the user 10 via the earpiece 16. The user 10 can also mark events and can call for start-stop-update by use of a sensor attached to the device 12, or alternatively on the body. Such events can also be activated by a trainer using a telemetry device, or can be undertaken automatically at set time intervals.

Figure 9:
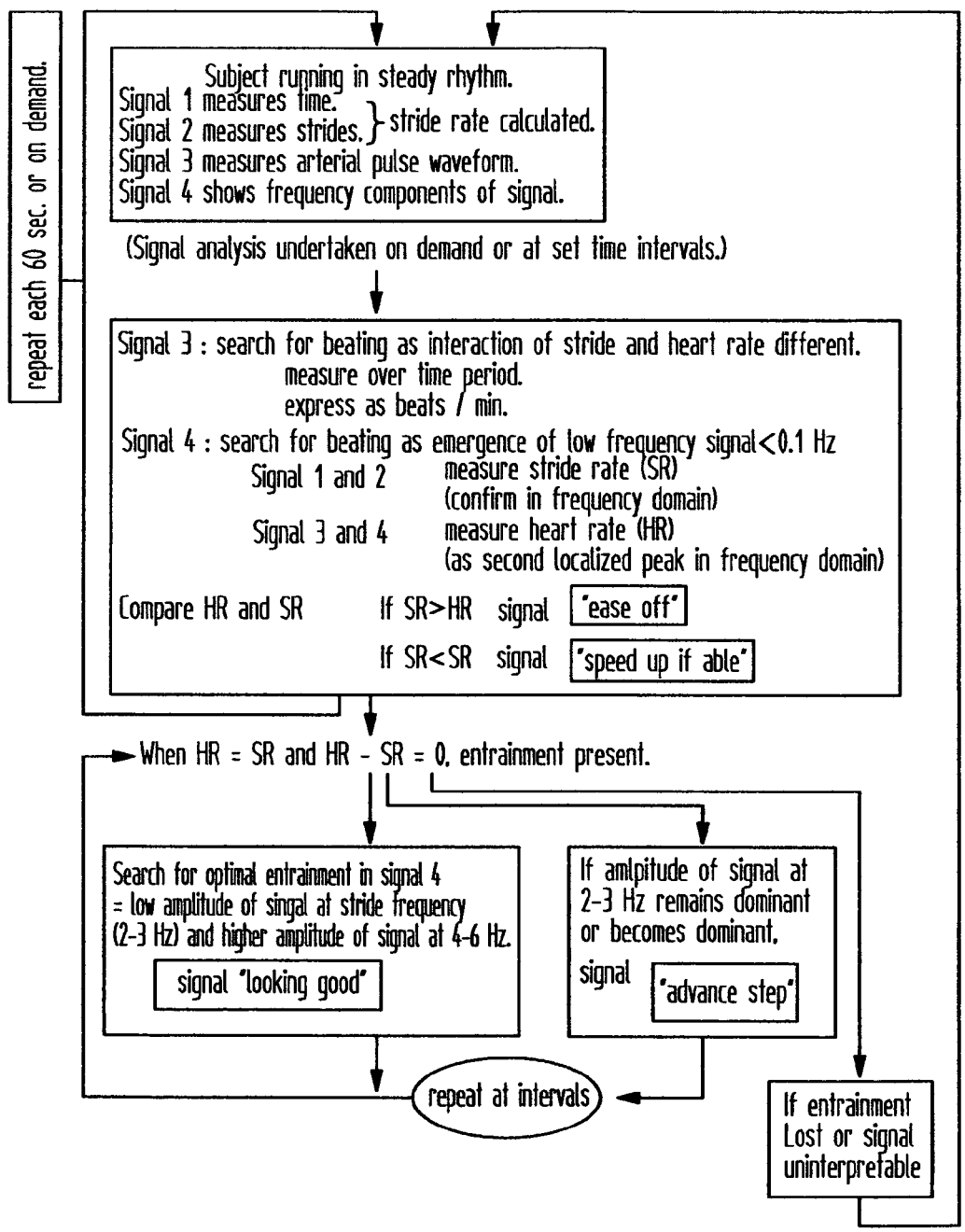
FIG. 9 is a logic diagram for the operation of a processor in the device shown in FIG. 1.

With the runner in a regular rhythm, the processor identifies the runner's dominant stride rate frequency from the pedometer and clock, in strides/min. This will normally be in the range of 2-3 Hz (120-180 strides/min). When the runner's dominant stride rate frequency is established, corresponding to the stride rate calculated from the pedometer and clock signals, the processor in the device 12 then determines other frequencies which are related to cardiac ejection by frequency spectrum analysis of the arterial pulse waveform. FIG. 9 shows the logic associated with the frequency spectrum analysis of the arterial pulse waveform of the processor in the device 12.

The processor also calculates the difference between the runner's stride rate dominant frequencies and the runner's pulse rate dominant frequencies by determining the beating frequency. Beating is readily apparent in the waveform signal (see FIG. 10). The waveforms are displayed in both the time and frequency domains either on the display screen of the device 12, or telemeted to a training screen.

Figure 6:
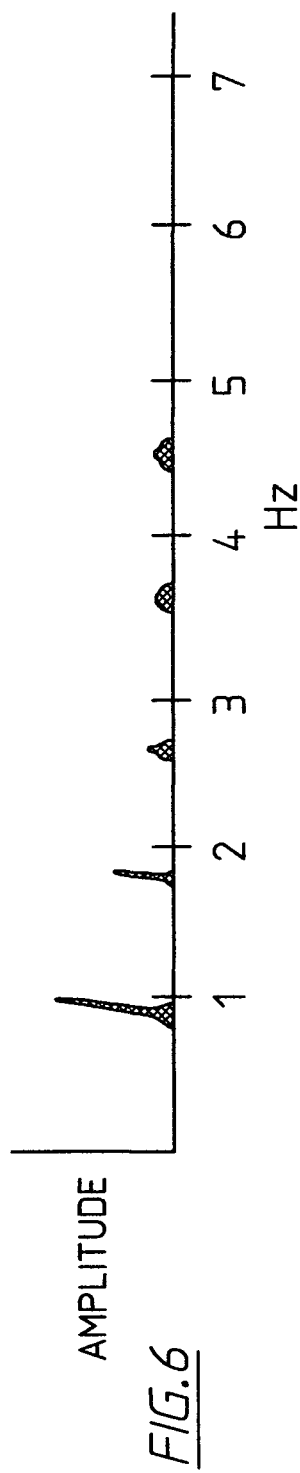
FIG. 6 is a plot of a person's arterial pulse waveform amplitude components at various frequencies whilst at rest.

From the situation at rest with the user 10 standing still, the arterial waveform is created by the heart alone and is characterised by components at multiples of heart frequency, as shown in FIGS. 3 and 6 respectively.

Figure 10:
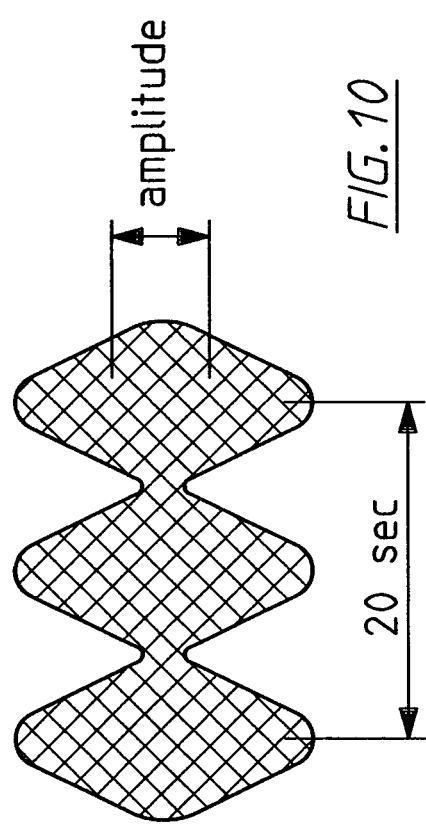
FIG. 10 is a is a plot of a person's arterial waveform pulse height, over a 20 second interval, just prior to entrainment occurring.
Figure 11:
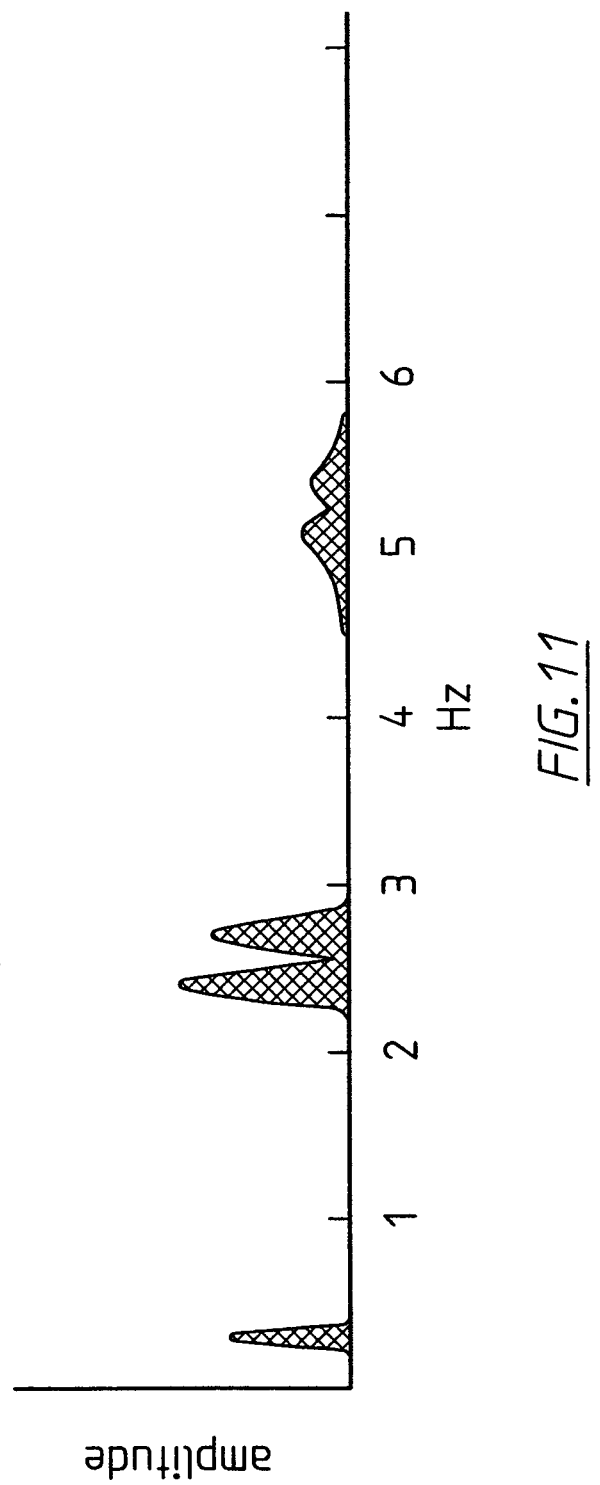
FIG. 11 is a plot of a person's arterial pulse waveform amplitude components at various frequencies just prior to entrainment occurring.

When running commences, a new arterial waveform emerges, which is independent of the heart rate and is caused by bodily movement. As shown in FIG. 10, interaction between the stride rate frequency and the pulse rate frequency is seen in the time domain as a beating pattern. As shown in FIG. 11, interaction between the stride rate frequency and the pulse rate frequency is seen in the frequency domain as a separation of frequency components at multiples of stride rate and pulse rate, together with the emergence of a frequency which corresponds to the difference between the stride rate and the pulse rate frequencies. The component in the frequency domain due to stride rate is identified from the stride rate calculated from the clock/pedometer data, so that the other peak is identifed as attributed to the pulse rate. If most energy in this localized frequency band is above the stride rate, the pulse rate is identified as >stride rate. The runner is advised to "speed up if possible" if the stride rate is less than the pulse rate, and to "ease off" if the stride rate is greater than the pulse rate (as shown in FIG. 9). The process is repeated until favourable entrainment is achieved.

Entrainment becomes apparent when the peaks of amplitude converge in the 2-3 Hz and in the 4-6 Hz range, and when there is no evidence of beating in the time domain or in the frequency domain.

The device 12 is activated by the runner, by a trainer, or automatically at intervals of 1-5 minutes. The device 12 performs the frequency spectrum analysis described above of recordings over a predetermined period (usually 30-60 seconds), and determines the stride rate frequency, and its amplitude, and compares the stride rate frequency with the other frequency components which are generated by the mechanical heart activity.

The information signalled to the user 10, and if desired a trainer, are the amplitude and frequency of the recorded waveforms. The processor determines that the user 10 is approaching entrainment when the frequency components become discrete in the frequency range of 2-3 Hz, and of 4-6 Hz, together with loss of the low frequency component corresponding to the difference between pulse rate and stride rate.

Entrainment is identified to the user 10 as being adverse (unfavourable) to their optimum training when the amplitude of the stride rate frequency component at 2-3 Hz is relatively large, and dominant over that at 4-6 Hz. This is shown in FIG. 7 and corresponds to the waveform shown in FIG. 4.

Entrainment is characterised to the user 10 as being optimal (favourable) for their training when the stride rate frequency component at 2-3 Hz is of low amplitude, and is dominated by the amplitude of the higher frequency components at 4-6 Hz. This is shown in FIG. 8. and corresponds to the waveform shown in FIG. 5.

In addition, the amplitude of the user's dominant pulse waveform whilst in the optimal relationship is minimal (e.g. less than about 33%) compared to the amplitude of the user's dominant pulse waveform whilst in the sub-optimal relationship.

Figure 7:
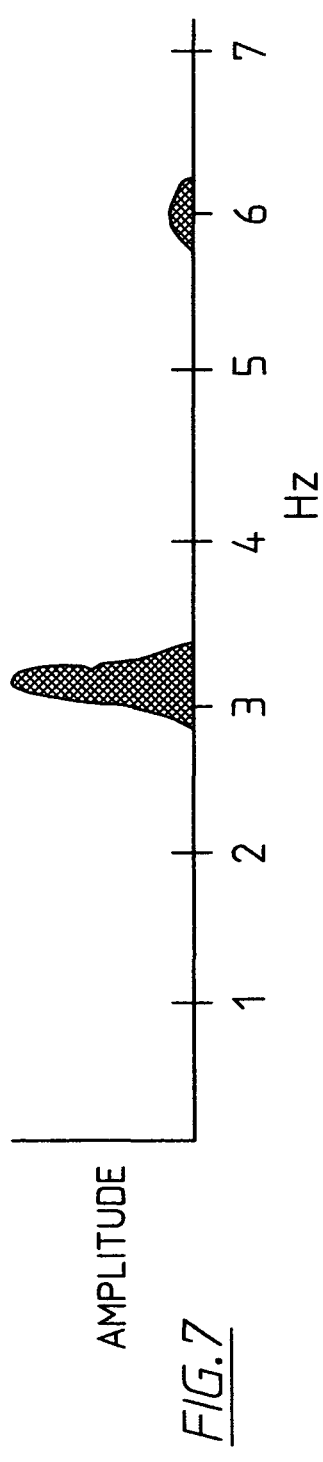
FIG. 7 is a plot of a person's arterial pulse waveform amplitude component at various frequencies whilst running when pulse rate and step rate are in an unfavourable phase at 3 Hz.
Figure 8:
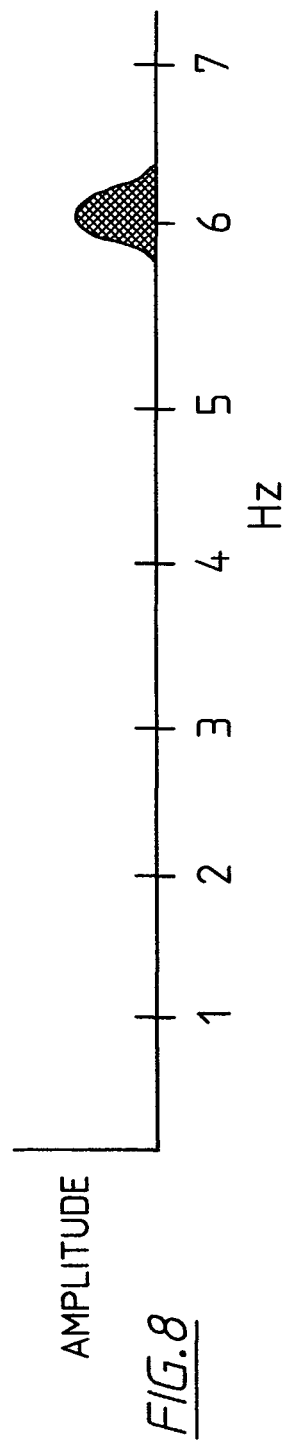
FIG. 8 is a plot of a person's arterial pulse waveform amplitude components at various frequencies whilst running when pulse rate and step rate are in a favourable phase at 3 Hz.

The frequency spectrums shown in FIGS. 6 to 8 are determined automatically, or on demand (by runner or trainer) at intervals of 1-3 minutes and are capable of display on a screen. Interpretation is performed automatically as described above, and the runner is advised by auditory prompts, either 1. "beating identified at x per min, stride rate 00 per min, greater than (or less than) heart rate"

or

2. "entrainment present, optimal"

or

3. "entrainment present, not favorable"

or

4. "signals not interpretable"

This message will be repeated until updated by further analysis at intervals of 1-3 minutes.

Easily interpretable training advice can also be embedded such as "in rhythm, looking good" for optimal entrainment or "ease off or advance step" for unfavourable entrainment, and communicated to the user 10 via the earpiece 16. The device 12 is thereby allows the user 10 to adjust their stride rate in real time whilst running, in order to optimize the favorable affects of entrainment, being minimal rise in arterial pressure while the ventricle is contracting, and minimal fall in arterial pressure during ventricular relaxation, when the coronary arteries are perfused.

LED's on other colored lights can also be used to indicate to entrainment conditions to the user 10, such as a green light for optimal and a red light for adverse sub-optimal. Other colours can also be used to indicate that the user should increase or decrease their stride rate to achieve favourable entrainment.

Although the invention has been described with reference to a preferred embodiment, it will be appreciated by those persons skilled in the art the invention may be embodied in many other forms.

The invention claimed is:

1. A step rate optimization device for a long distance runner, the device comprising:
    a timer adapted to measure a predetermined period of time and issue a first signal indicative thereof;
    a pedometer adapted to measure the number of a user's steps over the predetermined period of time and issue a second signal indicative thereof;

an arterial waveform sensor adapted to issue a third signal indicative of the user's arterial pulse waveform over the predetermined period of time;

a processor adapted to receive said first, second and third signals and determine and issue a fourth signal indicative of the relationship between the user's dominant stride rate frequency, the user's dominant pulse rate waveform frequency and the interaction of the user's dominant stride rate frequency and the user's dominant pulse rate waveform frequency in the range of approximately 0-8 Hz, wherein the processor is adapted to performs frequency spectrum analysis of the user's arterial pulse waveform and the user's dominant stride rate to identify entrainment status of the user; and an indicator adapted to communicate to the user an indication of an unfavorable entrainment relationship between the user's pulse rate and stride rate when the fourth signal indicates the user's dominant stride rate frequency to be at about 2-3 Hz and having a larger amplitude than the component of the user's dominant pulse waveform frequency at about 4-7 Hz and an indication of a favorable entrainment relationship between the user's pulse rate and stride rate when the fourth signal indicates the user's dominant stride rate frequency component to be at about 4-7 Hz and having a larger amplitude than the component of the user's dominant pulse waveform frequency at about 2-3 Hz;

wherein the processor is further adapted to determine whether the amplitude of the user's dominant pulse waveform whilst in the favorable entrainment relationship is less than the amplitude of the user's dominant pulse waveform whilst in the unfavorable entrainment relationship, and to determine that the amplitude of the user's dominant pulse waveform whilst in the favorable entrainment relationship is less than about 33% of the amplitude of the user's dominant pulse waveform whilst in the unfavorable entrainment relationship.

2. The device as claimed in claim 1, wherein the indicator is adapted to communicate to the user an indication of an unfavorable entrainment relationship between the user's pulse rate and stride rate when the fourth signal indicates the user's dominant stride rate frequency to be at about 3 Hz and having a larger amplitude than the component of the user's dominant pulse waveform frequency at about 6 Hz and an indication of a favorable entrainment relationship between the user's pulse rate and stride rate when the fourth signal indicates the user's dominant stride rate frequency component to be at about 6 Hz and having a larger amplitude than the component of the user's dominant pulse waveform frequency at about 3 Hz.

3. The device as claimed in claim 1, wherein the indicator is a visual indicator.

4. The device as claimed in claim 3, wherein the visual indicator is a display screen adapted to signal an unfavorable or favorable entrainment relationship.

5. The device as claimed in claim 3, wherein the visual indicator is a differently colored pair of lights each adapted to signal an unfavorable or favorable entrainment relationship respectively.

6. The device as claimed in claim 1, wherein the indicator is an aural indicator.

7. The device as claimed in claim 6, wherein the aural indicator is an ear-piece or other speaker.

8. The device as claimed in claim 1, wherein the user's arterial pulse waveform is measured at the upper body or an upper limb.

9. The device as claimed in claim 8, wherein the user's arterial pulse waveform is measured by a photo plethysmograph.

10. The device as claimed in claim 9, wherein the user's arterial pulse waveform is measured by the photo plethysmograph on a finger.

11. The device as claimed in claim 1, wherein the user's arterial pulse waveform is measured by an arterial tonometer.

12. The device as claimed in claim 11, wherein the user's arterial pulse waveform is measured by the arterial tonometer on a wrist.

13. The device as claimed in claim 12, wherein pressure, flow or diameter signals are used to determine the user's arterial pulse waveform frequency and amplitude.

14. The device as claimed in claim 1, wherein the predetermined period of time is about 30 seconds.

15. The device as claimed in claim 1, wherein the indicator displays modulus of frequency components over a range of 0.02-8.0 Hz.

16. The device as claimed in claim 1, wherein the device is adapted to continuously measure the predetermined period of time and continuously issue an indication of the entrainment relationship between the user's heart rate and stride rate.

* * * * *